(12) United States Patent
D'Souza

(10) Patent No.: US 11,524,058 B2
(45) Date of Patent: Dec. 13, 2022

(54) ORAL DISSOLVING FILMS CONTAINING MICROENCAPSULATED VACCINES AND METHODS OF MAKING SAME

(71) Applicant: THE CORPORATION OF MERCER UNIVERSITY, Macon, GA (US)

(72) Inventor: Martin J. D'Souza, Johns Creek, GA (US)

(73) Assignee: THE CORPORATION OF MERCER UNIVERSITY, Macon, GA (US)

( * ) Notice: Subject to any disclaimer, the term of this patent is extended or adjusted under 35 U.S.C. 154(b) by 151 days.

(21) Appl. No.: 17/034,858

(22) Filed: Sep. 28, 2020

(65) Prior Publication Data

US 2021/0015909 A1  Jan. 21, 2021

Related U.S. Application Data

(63) Continuation-in-part of application No. 16/017,542, filed on Jun. 25, 2018, now Pat. No. 10,786,558, which is a continuation of application No. 14/874,978, filed on Oct. 5, 2015, now Pat. No. 10,004,790, which is a continuation-in-part of application No. 12/569,867, filed on Sep. 29, 2009, now Pat. No. 9,149,441.

(60) Provisional application No. 61/100,886, filed on Sep. 29, 2008.

(51) Int. Cl.
| | | |
|---|---|---|
| A61K 39/00 | (2006.01) | |
| C12N 7/00 | (2006.01) | |
| A61K 39/165 | (2006.01) | |
| A61K 39/095 | (2006.01) | |
| A61K 9/00 | (2006.01) | |
| A61K 9/51 | (2006.01) | |
| A61K 31/245 | (2006.01) | |
| A61K 31/46 | (2006.01) | |
| A61K 31/5383 | (2006.01) | |
| A61K 31/7036 | (2006.01) | |
| A61K 31/7048 | (2006.01) | |
| A61K 31/7088 | (2006.01) | |
| A61K 31/727 | (2006.01) | |
| C12N 15/88 | (2006.01) | |
| A61K 9/16 | (2006.01) | |
| A61K 39/155 | (2006.01) | |
| A61K 48/00 | (2006.01) | |
| C12N 5/071 | (2010.01) | |

(52) U.S. Cl.
CPC ............ *A61K 39/00* (2013.01); *A61K 9/0021* (2013.01); *A61K 9/1652* (2013.01); *A61K 9/5161* (2013.01); *A61K 9/5169* (2013.01); *A61K 9/5192* (2013.01); *A61K 31/245* (2013.01); *A61K 31/46* (2013.01); *A61K 31/5383* (2013.01); *A61K 31/7036* (2013.01); *A61K 31/7048* (2013.01); *A61K 31/7088* (2013.01); *A61K 31/727* (2013.01); *A61K 39/0008* (2013.01); *A61K 39/0011* (2013.01); *A61K 39/095* (2013.01); *A61K 39/155* (2013.01); *A61K 39/165* (2013.01); *C12N 5/0677* (2013.01); *C12N 7/00* (2013.01); *C12N 15/88* (2013.01); *A61K 48/00* (2013.01); *A61K 2039/52* (2013.01); *A61K 2039/54* (2013.01); *A61K 2039/55555* (2013.01); *A61K 2039/55594* (2013.01); *A61K 2039/57* (2013.01); *C12N 2533/72* (2013.01); *C12N 2533/74* (2013.01); *C12N 2760/18434* (2013.01); *C12N 2760/18534* (2013.01)

(58) Field of Classification Search
None
See application file for complete search history.

(56) References Cited

U.S. PATENT DOCUMENTS

| | | |
|---|---|---|
| 3,137,631 A | 6/1964 | Soloway |
| 3,202,731 A | 8/1965 | Grevenstuk et al. |
| 3,429,827 A | 2/1969 | Ruus |
| 3,663,685 A | 5/1972 | Evans |
| 3,663,686 A | 5/1972 | Grotenhuis et al. |
| 3,663,687 A | 5/1972 | Evans |
| 3,758,678 A | 9/1973 | Lindsay et al. |
| 3,937,668 A | 2/1976 | Zolle |
| 3,962,414 A | 6/1976 | Michaels |
| 4,147,767 A | 4/1979 | Yapel, Jr. |
| 4,169,804 A | 10/1979 | Yapel, Jr. |

(Continued)

FOREIGN PATENT DOCUMENTS

| | | |
|---|---|---|
| JP | H09506109 A | 6/1997 |
| JP | H10506406 A | 6/1998 |

(Continued)

OTHER PUBLICATIONS

Abbott et al., Structure and function of the blood-brain barrier. Neurobiology of disease, 2010, pp. 13-25, vol. 37.

(Continued)

*Primary Examiner* — Anand U Desai
(74) *Attorney, Agent, or Firm* — Barnes & Thornburg LLP; Jason Bernstein

(57) ABSTRACT

An oral dissolving film containing nano- or micro-encapsulated bioactive material and methods of forming the film. The film may be prepared by dispensing a mixture of a film-forming agent, a crosslinking agent, a solution of nano- or micro-encapsulated bioactive material, and a photoinitiator into a plurality of wells in a tray using a 3D printer. The dispensed material is exposed to radiation in order to crosslink the material and form a film.

12 Claims, 9 Drawing Sheets

(56) References Cited

U.S. PATENT DOCUMENTS

| | | |
|---|---|---|
| 4,186,183 A | 1/1980 | Steck et al. |
| 4,230,687 A | 10/1980 | Sair et al. |
| 4,349,530 A | 9/1982 | Royer |
| 4,356,259 A | 10/1982 | Banba |
| 4,671,954 A | 6/1987 | Goldberg et al. |
| 4,674,480 A | 6/1987 | Lemelson |
| 4,680,174 A | 7/1987 | Jarvin, Jr. et al. |
| 4,764,359 A | 8/1988 | Lemelson |
| 4,925,661 A | 5/1990 | Huang |
| 4,963,367 A | 10/1990 | Ecanow |
| 5,017,379 A | 5/1991 | Lemelson |
| 5,069,936 A | 12/1991 | Yen |
| 5,129,877 A | 7/1992 | Gallo et al. |
| 5,690,954 A | 11/1997 | Illum |
| 6,117,454 A | 9/2000 | Kreuter et al. |
| 6,498,147 B2 | 12/2002 | Nerenberg et al. |
| 6,555,110 B1 | 4/2003 | D'Souza |
| 7,105,158 B1 | 9/2006 | D'Souza et al. |
| 8,053,000 B2 | 11/2011 | Srinivas et al. |
| 2001/0043949 A1 | 11/2001 | Delgado |
| 2002/0081336 A1 | 6/2002 | Jonsson et al. |
| 2002/0177568 A1 | 11/2002 | Stinchcomb et al. |
| 2003/0118653 A1* | 6/2003 | Chen ............... A61K 9/006 424/484 |
| 2004/0005569 A1 | 1/2004 | Baker et al. |
| 2004/0043079 A1 | 3/2004 | D'Souza |
| 2005/0089576 A1 | 4/2005 | Moreau |
| 2007/0078414 A1 | 4/2007 | McAllister et al. |
| 2008/0166414 A1 | 7/2008 | Hanes et al. |
| 2008/0269666 A1 | 10/2008 | Wang et al. |
| 2009/0047330 A1* | 2/2009 | Bangalore ......... A61K 9/006 424/443 |
| 2009/0081306 A1 | 3/2009 | D'Souza |
| 2009/0155330 A1 | 6/2009 | Ghartey-Tagoe et al. |
| 2010/0111984 A1 | 5/2010 | D'Souza |
| 2011/0121486 A1 | 5/2011 | Oh et al. |
| 2015/0112250 A1 | 4/2015 | Kwon |
| 2016/0058992 A1 | 3/2016 | Chen |
| 2016/0287668 A1 | 10/2016 | Tankovich |
| 2019/0060426 A1 | 2/2019 | D'Souza |

FOREIGN PATENT DOCUMENTS

| | | |
|---|---|---|
| JP | 2005513098 A | 5/2005 |
| JP | 2006511461 A | 4/2006 |
| WO | 9410980 A1 | 5/1994 |
| WO | 9522963 A1 | 8/1995 |
| WO | 9609814 A1 | 4/1996 |
| WO | 0002574 A1 | 1/2000 |
| WO | 03053413 A2 | 7/2003 |
| WO | 2008053481 A1 | 5/2008 |
| WO | 2009094394 A1 | 7/2009 |
| WO | 2012153266 A2 | 11/2012 |
| WO | 2016163753 A1 | 10/2016 |

OTHER PUBLICATIONS

Alimohammadi et al., Evidence for nicotinic acetylcholine receptors on nasal trigeminal nerve endings of the rat, Chemical senses, 2000, pp. 61-66, vol. 25.

Anand et al., Drug transporters in the nasal epithelium: an overview of strategies in targeted drug delivery, Future medicinal chemistry, 2014, pp. 1381-1397, vol. 6.

Ballabh et al., The blood-brain barrier: an overview: structure, regulation, and clinical implications, Neurobiology of disease, 2004, pp. 1-13, vol. 16.

Bhowmik et al., A novel microparticulale vaccine for melanoma cancer using transdermal delivery, J Microencapsul., May 17, 2011, vol. 28, No. 4, pp. 294-300.

Blesch et al., Transient growth factor delivery sustains regenerated axons after spinal cord injury, J Neurosci, 2007, pp. 10535-10545, vol. 27.

Bogdan et al., The role of nitric oxide in innate immunity, Immunological reviews, 2000, pp. 17-26, vol. 27.

Born et al., Sniffing neuropeptides: a transnasal approach to the human brain, Nat Neurosci, 2002, pp. 514-516, vol. 5.

Broadwell et al., Transcytosis of protein through the mammalian cerebral epithelium and endothelium. III. Receptor-mediated transcytosis through the blood-brain barrier of blood-borne transferrin and antibody against the transferrin receptor, Experimental neurology, 1996, pp. 47-65, vol. 142.

Broderick et al., Vascular risk factors and dementia: how to move forward?, Neurology, 2009, pp. 1934-1935, vol. 73.

Carson et al., A brief history of oxytocin and its role in modulating psychostimulant effects, Journal of psychopharmacology, 2013, pp. 231-247, vol. 27, Oxford, England.

Ceseracciu et al., Robust and biodegradable elastomers based on com starch and polydimethylsiloxane {PDMS), ACS Appl Maler Interfaces, Jan. 26, 2015, vol. 7, No. 6, pp. 3742-3753.

Chablani et al., Spray-dried microparticles: a potential vehicle for oral delivery of vaccines, J Microencapsul, 2012, pp. 388-397, vol. 29.

Crcarevska et al., Chitosan coated Ca-alginate microparticles loaded with budesonide for delivery to the inflamed colonic mucosa, European Journal of Pharmaceutics 2008, 68:565-578, Available online Jun. 14, 2007.

Curry et al., Separating the agony from ecstasy: R(-)-3,4-methylenedioxymethamphetamine has prosocial and therapeutic-like effects without signs of neurotoxicity in mice, Neuropharmacology, 2018, pp. 196-206, vol. 128.

Dal Monte et al., CSF and blood oxytocin concentration changes following intranasal delivery in macaque, PLoS One, 2014, e103677, vol. 9, No. 8.

Dawbarn et al., Neurotrophins and neurodegeneration, Neuropathology and applied neurobiology, 2003, pp. 211-230, vol. 29.

Donaldson et al., Oxytocin, vasopressin, and the neurogenetics of sociality, Science, 2008, pp. 900-904, vol. 322, New York, New York.

Dumont et al., Increased oxytocin concentrations and prosocial feelings in humans after ecstasy (3,4-methylenedioxymethamphetamine) administration, Soc Neurosci, 2009, pp. 359-366, vol. 4.

Engelmann et al., Behavioral consequences of intracerebral vasopressin and oxytocin: focus on learning and memory, Neurosci Biobehav Rev, 1996, pp. 341-358, vol. 20.

Etame et al., Design and potential application of PEGylated gold nanoparticles with size-dependent permeation through brain microvasculature, Nanomedicine : nanotechnology, biology, and medicine, 2011, pp. 992-1000, vol. 7.

Gan et al., Transferrin-conjugated nanoparticles of poly(lactide)-D-alpha-tocopheryl polyethylene glycol succinate diblock copolymer for targeted drug delivery across the blood-brain barrier, Biomaterials, 2010, pp. 7748-7757, vol. 31.

Gatter et al., Transferrin receptors in human tissues: their distribution and possible clinical relevance, Journal of clinical pathology, 1983, pp. 539-545, vol. 36.

Golde et al., A rapid, simple, and humane method for submandibular bleeding of mice using a lancet, Lab animal, 2005, pp. 39-43, vol. 34.

Gooding et al., Synthesis and characterization of rabies virus glycoprotein-tagged amphiphilic cyclodextrins for siRNA delivery in human glioblastoma cells: in vitro analysis, European journal of pharmaceutical sciences: official journal of the European Federation for Pharmaceutical Sciences, 2015, pp. 80-92, vol. 71.

Hanada et al., Cell-based in vitro blood-brain barrier model can rapidly evaluate nanoparticles' brain permeability in association with particle size and surface modification, International journal of molecular sciences, 2014, pp. 1812-1825, vol. 15.

Harris et al., Subjective and hormonal effects of 3,4-methylenedioxymethamphetamine (MDMA) in humans, Psychopharmacology, 2002, pp. 396-405, vol. 162.

Haswani et al.; Formulation, Characterization and Pharmacokinetic Evaluation of Gentamicin Sulphate Loaded Albumin Microspheres; Journal of Microencapsulation; Dec. 2006; vol. 23, No. 8; pp. 875-886.

(56) References Cited

OTHER PUBLICATIONS

He et al., Immortalized mouse brain endothelial cell line Bend.3 displays the comparative barrier characteristics as the primary brain microvascular endothelial cells, Zhongguo dang dai er ke za zhi (Chinese journal of contemporary pediatrics), 2010, pp. 474-478, vol. 12.
Herrmann et al., Current and emerging drug treatment options for Alzheimer's disease: a systematic review, Drugs, 2011, pp. 2031-2065, vol. 71.
Huang et al.; The Characteristics Of Betamethasone-Loaded Chitosan Microparticles By Spray-Drying Method Journal of Microencapsulation; vol. 20, No. 4; July/Aug. 2003; pp. 459-472.
International Preliminary Reporton Patentability for International Patent Application No. PCT/US2017/061353; dated May 14, 2019.
Jones et al., Spray-dried doxorubicin-albumin microparticulate systems for treatment of multidrug resistant melanomas, Journal of drug targeting, 2011, pp. 427-433, vol. 19.
Keech et al., Intranasal oxytocin, social cognition and neurodevelopmental disorders: A meta-analysis, Psychoneuroendocrinology, 2018, pp. 9-19, vol. 87.
Keiger et al. Nicotinic cholinergic receptor expression in the human nasal mucosa, The Annals of otology, rhinology, and laryngology, 2003, pp. 77-84, vol. 112.
Kim et al., Brain-targeted delivery of protein using chitosan- and RVG peptide-conjugated, pluronic-based nano-carrier, Biomaterials, 2013, pp. 1170-1178, vol. 34.
Klemp et al., Repeated inhibitory effects of NPY on hippocampal CA3 seizures and wet dog shakes, Peptides, 2001, pp. 523-527, vol. 22.
Kolluru et al., Formulation development of albumin based theragnostic nanoparticles as a potential delivery system for tumor targeting, Journal of drug targeting, 2013, pp. 77-86, vol. 21.
Kou et al., The endocytosis and intracellular fate of nanomedicines: Implication for rational design, Asian Journal of Pharmaceutical Sciences, 2013, pp. 1-10, vol. 8.
Kulkarni et al. Effects of particle size and surface modification on cellular uptake and biodistribution of polymeric nanoparticles for drug delivery, Pharmaceutical research, 2013, pp. 2512-2522, vol. 30.
Kumar et al., Transvascular delivery of small interfering RNA to the central nervous system, Nature, 2007, pp. 39-43, vol. 448.
Lafay et al., Spread of the CVS strain of rabies virus and of the avirulent mutant AvO1 along the olfactory pathways of the mouse after intranasal inoculation, Virology, 1991, pp. 320-330, vol. 183.
Leng et al., Intranasal Oxytocin: Myths and Delusions, Biol Psychiatry, 2016, pp. 243-250, vol. 79.
Li et al., Nanoparticles bearing polyethyleneglycol-coupled transferrin as gene carriers: preparation and in vitro evaluation. International journal of pharmaceutics, 2003, pp. 93-101, vol. 259.
Li et al., Transepithelial electrical measurements with the Ussing chamber, Journal of cystic fibrosis: official journal of the European Cystic Fibrosis Society, 2004, pp. 123-126, vol. 3, Suppl. 2.
Liu et al., A technique for serial collection of cerebrospinal fluid from the cistema magna in mouse, Journal of visualized experiments (JoVE), 2008; p. 960, vol. 21.
Liu et al., Brain-targeted co-delivery of therapeutic gene and peptide by multifunctional nanoparticles in Alzheimer's disease mice, Biomaterials, 2016, pp. 33-45, vol. 80.
Makadia et al., Poly Lactic-co-Glycolic Acid (PLGA) as Biodegradable Controlled Drug Delivery Carrier, Polymers, 2011, pp. 1377-1397, vol. 3.
Mann et al., Transferrin conjugation confers mucosal molecular targeting to a model HIV-1 trimeric gp140 vaccine antigen, Journal of controlled release : official journal of the Controlled Release Society, 2012, pp. 240-249, vol. 158.
Misra et al., Drug delivery to the central nervous system: a review, Journal of pharmacy & pharmaceutical sciences : a publication of the Canadian Society for Pharmaceutical Sciences (Societe canadienne des sciences pharmaceutiques), 2003, pp. 252-273, vol. 6.

Wuest et al., Membrane configuration optimization for a murine in vitro blood-brain barrier model, J Neurosci Methods, 2013, pp. 211-221, vol. 212.
Yan et al., Transferrin-conjugated, fluorescein-loaded magnetic nanoparticles for targeted delivery across the blood-brain barrier, Journal of materials science Materials in medicine, 2013, pp. 2371-2379, vol. 24.
Yeung et al., Membrane phosphatidylserine regulates surface charge and protein localization, Science, 2008, pp. 210-213, vol. 319, New York, New York.
Ying et al., Dual-targeting daunorubicin liposomes improve the therapeutic efficacy of brain glioma in animals, Journal of controlled release : official journal of the Controlled Release Society, 2010, pp. 183-192; vol. 141.
Zhang et al., Transferrin receptor targeted lipopolyplexes for delivery of antisense oligonucleotide g3139 in a murine k562 xenograft model, Pharmaceutical research, 2009, pp. 1516-1524, vol. 26.
Zughaier et al., Antimicrobial peptides and endotoxin inhibit cytokine and nitric oxide release but amplify respiratory burst response in human and murine macrophages, Cellular microbiology, 2005, pp. 1251-1262; vol. 7.
Modi et al. Aerosolized oxytocin increases cerebrospinal fluid oxytocin in rhesus macaques, Psychoneuroendocrinology, 2014, pp. 49-57, vol. 45.
Modi et al., The oxytocin system in drug discovery for autism: animal models and novel therapeutic strategies, Horm Behav, 2012, pp. 340-350, vol. 61.
Montesano et al., Increased proteolytic activity is responsible for the aberrant morphogenetic behavior of endothelial cells expressing the middle T oncogene. Cell, 1990, pp. 435-445, vol. 62.
Morley et al., Serotonin (1A) receptor involvement in acute 3,4-methylenedioxymethamphetamine (MDMA) acilitation of social interaction in the rat, Prog Neuropsychopharmacol Biol Psychiatry, 2005, pp. 648-657, vol. 29.
Murnane et al., Endocrine and neurochemical effects of 3,4-methylenedioxymethamphetamine and its stereoisomers in rhesus monkeys, J Pharmacol Exp Ther, 2010, pp. 642-650, vol. 334.
Murnane et al., The neuropharmacology of prolactin secretion elicited by 3,4-methylenedioxymethamphetamine ("ecstasy"): a concurrent microdialysis and plasma analysis study, Horm Behav, 2012, pp. 181-60, vol. 61.
Nagahara et al., Neuroprotective effects of brain-derived neurotrophic factor in rodent and primate models of Alzheimer's disease, Nature medicine, 2009, pp. 331-337, vol. 15.
Nasatto et al., Methylcellulose, a cellulose derivative with original physical properties and extended applications, Polymers, Apr. 24, 2015, vol. 7, pp. 777-803.
Notification of Reasons for Refusal Translation, dated Dec. 24, 2013, JP Patent Application No. 2011-529378.
Notification of Reasons for Refusal translation: JP Patent Application No. 2011-529378; dated Dec. 24, 2013.
O'Brien et al., Amyloid precursor protein processing and Alzheimer's disease, Annu Rev Neurosci, 2011, pp. 185-204, vol. 34.
Oettinger et al., Pro-inflammatory cytokine inhibition in the primate using microencapsulated antisense oligomers tc NF-kappaB, J Microencapsul, 2007, pp. 337-348, vol. 24.
Opal et al., Anti-inflammatory cytokines, Chest, 2000, pp. 1162-1172, vol. 117.
Pan et al., Cationic lipid-coated magnetic nanoparticles associated with transferrin for gene delivery, International journal of pharmaceutics, 2008, pp. 263-270, vol. 358.
Pang et al., Enhanced intracellular delivery and chemotherapy for glioma rats by transferrin-conjugated biodegradablE polymersomes loaded with doxorubicin, Bioconjugate chemistry, 2011, pp. 1171-1180, vol. 22.
Pardridge, Blood-brain barrier delivery, Drug discovery today, 2007, pp. 54-61, vol. 12.
Pardridge, Blood-brain barrier drug delivery of IgG fusion proteins with a transferrin receptor monoclonal antibody, Expert opinion on drug delivery, 2014, pp. 1-16.
Prego et al., Chitosan-PEG nanocapsules as new carriers for oral peptide delivery: Effect of chitosan pegylation degree, Journal of Controlled Release, 2006, 111 :299-308.

(56) References Cited

OTHER PUBLICATIONS

Pulicherla et al., Targeting therapeutics across the blood brain barrier (BBB), prerequisite towards thrombolytic herapy for cerebrovascular disorders-an overview and advancements, AAPS PharmSciTech, 2015, pp. 223-233, vol. 16.
Qian et al., Targeted drug delivery via the transferrin receptor-mediated endocytosis pathway, Pharmacol Rev, 2002, pp. 561-587, vol. 54.
Reibel et al., Neuropeptide Y and epilepsy: varying effects according to seizure type and receptor activation, Peptides, 2001, pp. 529-539, vol. 22.
Robertson et al., Immunoassay of plasma vasopressin, Man. Proc Nall Acad Sci USA, 1970, pp. 1298-1305; vol. 66.
Sahoo et al., Enhanced antiproliferative activity of transferrin-conjugated paclitaxel-loaded nanoparticles is mediated a sustained intracellular drug retention, Molecular pharmaceutics, 2005, pp. 373-S3, vol. 2.
Saraiva et al., Nanoparticle-mediated brain drug delivery: Overcoming blood-brain barrier to treat neurodegenerative :liseases. Journal of controlled release : official journal of the Controlled Release Society, 2016, pp. 34-47, vol. 235.
Sullivan et al.: "Dissolving polymer microneedle patches for influenza vaccination", Nature Medicine, vol. 16, No. 8, Aug. 1, 2010 (Aug. 1, 2010), pp. 915-920, XP055568344, New York ISSN: 1078-8956, DOI: 10.1038/nm.2182 * p. 915, col. 2, paragraph 4—p. 916, col. 1, paragraph 1*.
Search Report and Written Opinion from International Application No. PCT/US2016/55515; dated Jan. 24, 2017.
Search Report for European Patent Application No. 17869270.3; dated Apr. 29, 2020.
Search Report for International Patent Application No. PCT/US2017/061353; dated Jan. 29, 2018.
Shastri et al., Implementation of mixture design for formulation of albumin containing enteric-coated spray-dried microparticles, Drug development and industrial pharmacy, 2013, pp. 164-175, vol. 39.
Sikorski et al., The Peyer's patch high endothelial receptor for lymphocytes, the mucosal vascular addressin, is nduced on a murine endothelial cell line by tumor necrosis factor-alpha and IL-1, Journal of immunology, 1993, pp. 5239-5250; vol. 151, Baltimore, Maryland.
Sloane et al., Anti-inflammatory cytokine gene therapy decreases sensory and motor dysfunction in experimental Multiple Sclerosis: MOG-EAE behavioral and anatomical symptom treatment with cytokine gene therapy, Brain, behavior, and immunity, 2009, pp. 92-100, vol. 23.
Soderquist et al., Central nervous system delivery of large molecules: challenges and new frontiers for intrathecall. administered therapeutics, Expert opinion on drug delivery, 2010, pp. 285-293, vol. 7.
Son et al., RVG peptide tethered bioreducible polyethylenimine for gene delivery to brain, Journal of controlled elease : official journal of the Controlled Release Society, 2011, pp. 18-25, vol. 155.
Sonavane et al., Biodistribution of colloidal gold nanoparticles after intravenous administration: effect of particle size, :;olloids and surfaces B, Biointerfaces, 2008, pp. 274-280, vol. 66.
Srinivasan et al., TEER measurement techniques for in vitro barrier model systems, Journal of laboratory ?utomation, 2015, pp. 107-126, vol. 20.
Strecker et al., Parkinson's disease: emerging pharmacotherapy, Expert opinion on emerging drugs, 2008, pp. 573-591, vol. 13.
Striepens et al., Elevated cerebrospinal fluid and blood concentrations of oxytocin following its intranasal administration in humans, Scientific reports, 2013, p. 3440, vol. 3.
Sundaram et al., Surface-functionalized nanoparticles for targeted gene delivery across nasal respiratory epithelium, Faseb j, 2009, pp. 3752-3765, vol. 23.
Supplementary European Search Report for European Patent Application No. EP 09 81 7062, filed Sep. 29, 2009, dated Mar. 20, 2013.
Tan et al., The influence of size, shape and vessel geometry on nanoparticle distribution, Microfluidics and nanofluidics, 2013, pp. 77-87; vol. 14.
Terryn et al., Protective effect of different anti-rabies virus VHH constructs against rabies disease in mice, PLoS One, 2014, e109367, vol. 9, No. 10.
Thompson et al., A role for oxytocin and 5-HT(1A) receptors in the prosocial effects of 3,4 methylenedioxymethamphetamine ("ecstasy"), Neuroscience, 2007, pp. 509-514, vol. 146.
Tong et al. Evaluation of PLGA microspheres as delivery system for antitumor agent-camptothecin, Drug evelopment and industrial pharmacy, 2003, pp. 745-756, vol. 29.
Truong et al., The importance of nanoparticle shape in cancer drug delivery, Expert opinion on drug delivery, 2015, pp. 129-142, vol. 12.
Ulbrich et al., Transferrin- and transferrin-receptor-antibody-modified nanoparticles enable drug delivery across the blood-brain barrier (BBB), European journal of pharmaceutics and biophanmaceutics : official journal of 1 \rbeitsgemeinschafl fur Pharmazeutische Verfahrenstechnik eV, 2009, pp. 251-256, vol. 71.
Walker et al., Anti-inflammatory and immune therapy for Alzheimer's disease: current status and future directions, Current neurophanmacology, 2007, pp. 232-243, vol. 5.
Watanabe et al., Paracellular barrier and tight junction protein expression in the immortalized brain endothelial cell ines bEND.3, bEND.5 and mouse brain endothelial cell 4, Biological & pharmaceutical bulletin, 2013, pp. 492-495, vol. 36.
Wiley et al., Transcytosis and brain uptake of transferrin-containing nanoparticles by tuning avidity to transferrin receptor, Proc Natl Acad Sci USA, 2013, pp. 8662-8667, vol. 110.
Williams et al., Embryonic lethalities and endothelial tumors in chimeric mice expressing polyoma virus middle T Jncogene, Cell, 1988, pp. 121-131, vol. 52.
Woldbye, Antiepileptic effects of NPY on pentylenetetrazole seizures, Regulatory peptides, 1998, pp. 279-282, vol. 75-76.
Office Action for European Patent Application No. 17869270.3; dated Apr. 22, 2021.

* cited by examiner

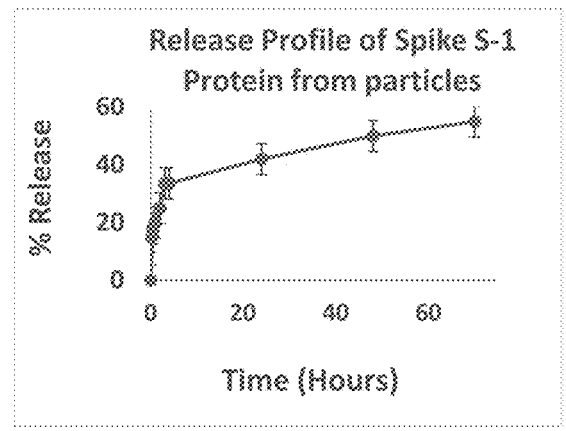
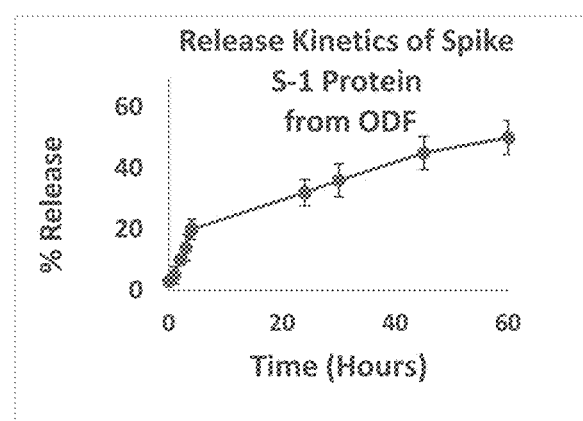
FIG. 8A  FIG. 8B
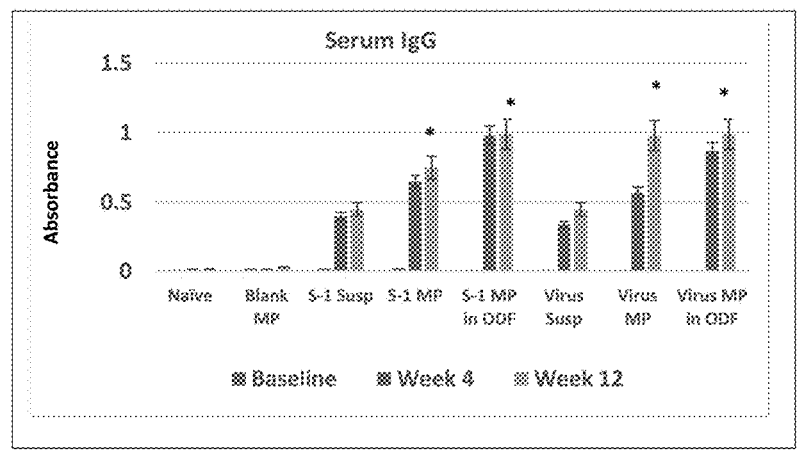
FIG. 9

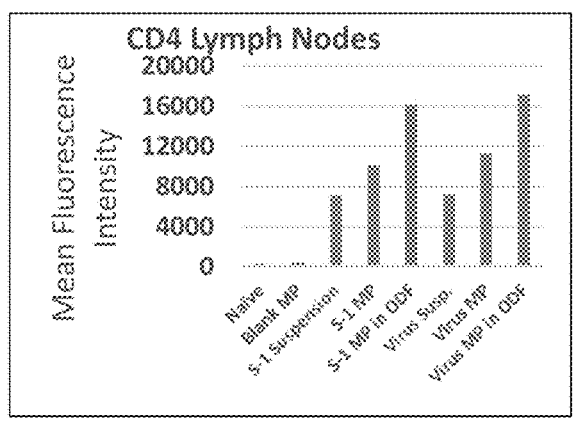 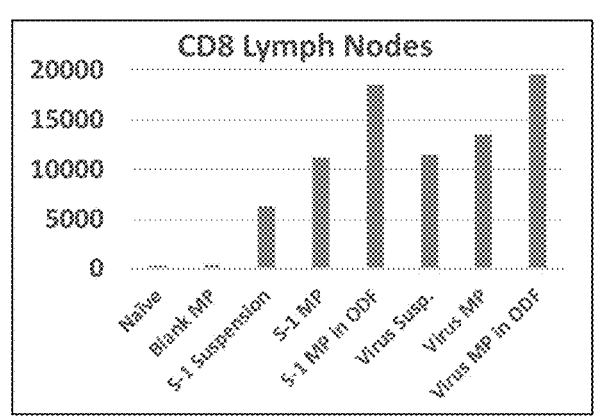
FIG. 10A                    FIG. 10B

ORAL DISSOLVING FILMS CONTAINING MICROENCAPSULATED VACCINES AND METHODS OF MAKING SAME

CROSS-REFERENCE TO RELATED APPLICATIONS

This application is a continuation-in-part of U.S. patent application Ser. No. 16/017,542, filed Jun. 25, 2018, entitled ORAL DISSOLVING FILMS, which is a continuation of U.S. patent application Ser. No. 14/874,978, filed Oct. 5, 2015, now U.S. Pat. No. 10,004,790, which is a continuation-in-part of U.S. patent application Ser. No. 12/569,867, filed Sep. 29, 2009, now U.S. Pat. No. 9,149,441, which claims the benefit of U.S. Provisional Patent Application No. 61/100,886, filed Sep. 29, 2008, and commonly assigned to the assignee of the present application, the disclosures of which are incorporated by reference in their entireties herein.

FIELD

The present disclosure relates, in exemplary embodiments, to oral dissolving films containing microencapsulated vaccines, drugs, or other bioactive materials, and methods for making same. More particularly, in exemplary embodiments methods are disclosed for printing oral dissolving films containing microencapsulated vaccines, drugs, or other bioactive materials using a 3D printer. Such films may be used, for example, for buccal or sublingual delivery of such materials.

BACKGROUND

Coronaviruses belong to a large family of viruses that are responsible for causing mild to severe upper respiratory tract illnesses in both animals as well as humans. These viruses thrive among animals and on occasion cross borders infecting humans. In recent months, there has been an emergence of a novel coronavirus global pandemic strain, SARS CoV-2 virus, which causes the disease COVID-19. Considering the similarity in the structure of different coronaviruses, the effectiveness of an oral dissolving film (ODF) formulation containing heat inactivated coronavirus and its ability to elicit an innate and adaptive immune response was tested. The heat inactivated virus is non-cytotoxic in addition to being immunogenic. Furthermore, the addition of adjuvants, such as, but not limited to, alum and MF59, to the vaccine can enhance the overall immune response to the antigen.

The buccal mucosa provides a unique site for very efficient drug delivery and vaccination, as it is easily accessible, and is a rich source of blood supply and immune cells. From a drug deliver standpoint, the rich blood supply results in quick absorption of the drug from the ODF, bypassing the deleterious metabolism effect of the liver (first pass effect) that metabolizes a high proportion of drugs that are administered as tablets and capsules. From a vaccine standpoint, the buccal cavity is the first line of defense against various pathogens including SARS and is equipped with the mucosal associated lymphoid tissues (MALT) to combat against invading pathogens. The buccal mucosa contains antigen presenting cells such as macrophages and dendritic cells. These are professional phagocytic cells that play an important role in immune surveillance and further signaling of T cells. Activated macrophages and T cells drain into draining lymph nodes (DLN) leading to an enhanced immune response. Thus, formulating a buccal mucosal vaccine is an effective method to protect from pathogens including the SARS virus and most other viruses and bacteria that enter the body through the oral cavity.

Current conventional vaccines involve administering the vaccine using needles by intramuscular, intra dermal or subcutaneously by trained personnel. These have been highly effective in generating protective immunity, but are painful, require cold chain storage, and require a skilled professional for vaccination. Also, vaccination with hypodermic needle injections are associated with logistical disadvantages including needle injuries and opportunistic infections, increasing the risk of hepatitis, HIV and other serious diseases that are transmitted by syringes and needles. Some side effects, including facial paralysis were reported to be associated with intranasal influenza vaccination with an inactivated virosomal vaccine formulated bacterial toxin or even in the absence of adjuvant.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to the more detailed description below.

Generally described, the present disclosure provides in exemplary embodiments a method of producing oral dissolving films containing at least one nano- or micro-encapsulated bioactive material, the method comprising the steps of: (a) preparing a solution of at least one film-forming agent, at least one crosslinking agent, and at least one polar solvent; (b) adding to the solution of step (a) either a suspension or solution of at least one microencapsulated bioactive material to form a mixture; (c) adding to the mixture of step (b) at least one surfactant and at least one photoinitiator to form a mixture; (d) dispensing the mixture of step (c) by a 3D printer into a tray having at least one well formed therein; and, (e) exposing the tray to radiation to initiate crosslinking so as to promote formation of a film in each well.

Also disclosed is an oral dissolving film containing nano- or micro-encapsulated bioactive material and methods of forming the film. The film may be prepared by dispensing a mixture of a film-forming agent, a crosslinking agent, a solution of nano- or micro-encapsulated bioactive material, and a photoinitiator into a plurality of wells in a tray using a 3D printer. The dispensed material is exposed to radiation in order to crosslink the material and form a film.

Also disclosed is a material for delivering at least one drug, vaccine, or other bioactive material, comprising: an oral dissolving film comprising a microencapsulated bioactive material, the film prepared according to one of the exemplary methods disclosed herein.

Other features will become apparent upon reading the following detailed description of certain exemplary embodiments, when taken in conjunction with the appended claims.

BRIEF DESCRIPTION OF THE DRAWINGS

The drawings disclose exemplary embodiments in which like reference characters designate the same or similar parts throughout the Figures of which:

FIG. 1 is a schematic view of an exemplary 3D printer (Cellink Incredible Plus, available from Cellink Inc. Sweden).

FIG. 7A is a chart showing The expression of antigen presenting and co-stimulatory molecules on Dendritic Cells post exposure to vaccines where MHC I and CD80 expression by Spike S-1 protein.

FIG. 7B is a chart showing The expression of antigen presenting and co-stimulatory molecules on Dendritic Cells post exposure to vaccines where MHC II and CD40 expression by Spike S-1 protein.

FIG. 7C is a chart showing The expression of antigen presenting and co-stimulatory molecules on Dendritic Cells post exposure to vaccines where MHC I and CD80 expression by SARS-CoV-2 virus.

FIG. 7D is a chart showing The expression of antigen presenting and co-stimulatory molecules on Dendritic Cells post exposure to vaccines where MHC II and CD40 expression by SARS-CoV-2 virus.

FIG. 8A is a graph of the release profile of the Spike S-1 protein from particles.

FIG. 8B is a graph of the release kinetcis of the Spike protein from the ODF.

FIG. 9 is a chart of Spike S-1 and SARS-CoV-2 Heat Inactivated Virus induced serum IgG levels. The mice received one vaccine dose at week 0. Either as the antigen in suspension/solution or in microparticles or microparticles in ODF. Serum IgG was determined at week 4 and 12. The ODF group receiving particulate vaccines showed IgG levels significantly higher than the corresponding suspension vaccinated mice ($*p<0.01$ from suspension group). [S-1=SARS CoV-2 Spike S-1 protein; Susp.=SARS CoV-2 Virus Suspension; MP=Microparticles, ODF=oral dissolving film].

FIG. 10A is a chart of CD4 T cell responses in lymph nodes obtained after sacrificing the mice at the end of the study in the ODF SARS CoV-2 Spike S-1 and ODF SARS Virus vaccine study.

FIG. 10B is a chart of CD8 T cell responses in lymph nodes obtained after sacrificing the mice at the end of the study in the ODF SARS CoV-2 Spike S-1 and ODF SARS Virus vaccine study. Both CD4 and CD8 responses were highest in the ODF formulations in the Spike and Virus studies.

Figures 11A, 11B:
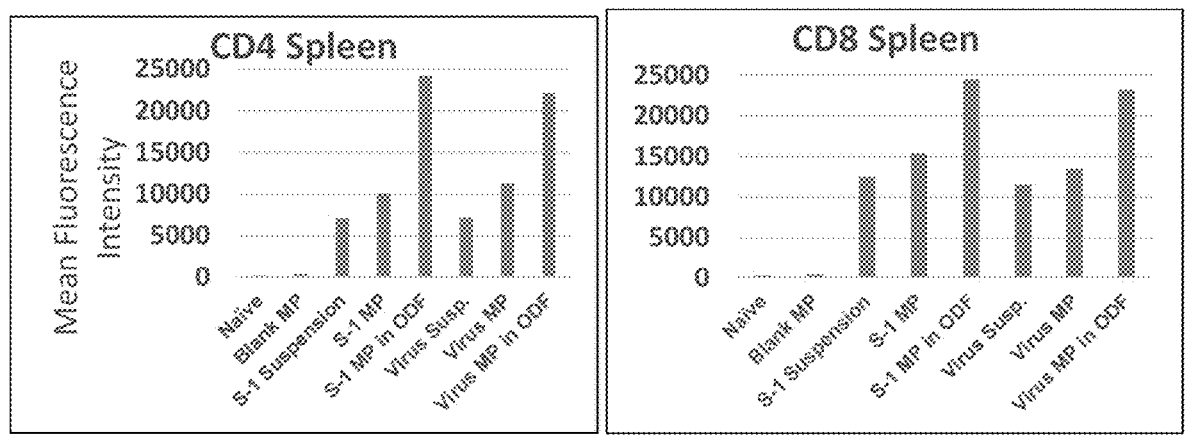

FIG. 11A is a chart of CD4 T cell responses in the spleen obtained after sacrificing the mice at the end of the study in the SARS CoV-2 Spike S-1 and ODF SARS CoV-2 virus vaccine study.

FIG. 11B is a chart of CD8 T cell responses in the spleen obtained after sacrificing the mice at the end of the study in the SARS CoV-2 Spike S-1 and ODF SARS CoV-2 virus vaccine study. Both CD4 and CD8 responses were highest in the ODF formulations in the Spike and Virus studies.

DETAILED DESCRIPTION

Unless otherwise indicated, the drawings are intended to be read (for example, cross-hatching, arrangement of parts, proportion, degree, or the like) together with the specification, and are to be considered a portion of the entire written description of this invention. As used in the following description, the terms "horizontal", "vertical", "left", "right", "up" and "down", "upper" and "lower" as well as adjectival and adverbial derivatives thereof (for example, "horizontally", "upwardly", or the like), simply refer to the orientation of the illustrated structure as the particular drawing Figure faces the reader. Similarly, the terms "inwardly" and "outwardly" generally refer to the orientation of a surface relative to its axis of elongation, or axis of rotation, as appropriate.

While drugs and vaccines are described herein, and occasionally referred to as "bioactive" material, the present disclosure anticipates that other materials may be used in the methods, formulations, and materials described herein, including, but not limited to, proteins, peptides, antibodies (whole or fragments thereof), enzymes, chemical entities, and the like, as well as steroids, immunosuppressants, nutritional supplements, and the like, and combinations of the foregoing. The terms drug and vaccine as used herein generally, are intended to also include other bioactive material.

It is intended that the oral dissolving films and methods of their production described herein with regard to a drug or vaccine are intended to also include the possibility of the incorporation of one or more drugs, vaccines, bioactive materials, or combinations of the foregoing, either by each being nano- or micro-encapsulated by itself and a mixture of encapsulated particles being in the oral dissolving film formulation, or, a combination of a plurality of different bioactive materials being so encapsulated in one particle.

Formulation and testing of novel a) COVID-19 SARS CoV-2 inactivated virus and b) Spike S-1 protein vaccine in oral dissolving films (ODF).

Introduction:

To enhance patient compliance and to eliminate painful needle administration, a novel ODF formulation was selected for delivering coronavirus antigen. The ODF patches allow self-administration of the vaccine which highly favors the current demand for mass vaccination.

In an attempt to overcome these limitations, we have explored the potential of delivering vaccine antigens using oral dissolving film (ODF) formulations skin. ODF delivery as proposed, is an attractive mode of immunization because of its ease of administration, and acceptability. Further, since the proposed vaccine exists in a dry form, it is thus well protected from moisture. Thus, the shelf lives of these vaccines are expected to be significantly higher than the conventional vaccines, without preservatives and/or refrigerating storage systems. This is especially relevant in developing countries where the cold-chain cannot be easily maintained. Here, we propose improved vaccine formulations that stabilize vaccines with encapsulating biopolymers that can be administered as an ODF formulation via the buccal or sublingual method. The novel vaccine encapsulated with SARS Spike S-1 protein or the heat inactivated SARS-CoV-2 virus incorporated into an albumin-based particulate matrix or poly lactic acid co glycolic acid (50:50 ratio), may provide the following advantages:

Whole-virus based vaccine encompasses all immunogenic epitopes;

Spike subunit S-1 protein is highly antigenic;

Self-adjuvanting vaccine formulations enhance immunogenicity with the addition of adjuvants that are toll like receptor (TLR) ligands such as Alum, MF59, MPL-A, Resiquimod, Imiquimod, CpG;

Improved uptake by immune cells and slow antigen release, i.e., "intracellular antigen depot effect," can result in prolonged cross-presentation in the lymph nodes and spleen, which is critical for T-cell stimulation;

Induction of robust autophagy formation that enhances antigen presentation;

Heat-stable formulation that does not require cold chain conditions;

Administration by an ODF formulation which is non-invasive, needle-free and pain-free; and Reduced cost with the elimination of expenditures relating to refrigeration of ampoules.

In terms of translatability to humans, as a clinically relevant and important vaccine strain, we will use the 2019 pandemic SARS-CoV-2 virus strain in vaccine challenge studies in hACE-2 transgenic mice and in ferrets.

The immune response is controlled through the coordination of the two major components of the immune system: the innate immune system and the adaptive immune system. The innate immune system is body's first line of defense mechanism. The components of the innate immune system include phagocytes and antigen presenting cells. The antigen presenting cells (APCs) including dendritic cells and macrophages forms the link between the innate and the adaptive immune response. The APCs process the antigen and present the antigenic proteins to the cells of the adaptive immune system to elicit a stronger and longer lasting immune response and create an immunological memory.

Antigens can be classified as exogenous or endogenous. Exogenous denotes that the antigen enters the host from an external environment (i.e., parenteral injection) and endogenous denotes that the antigen is generated within the host cell (i.e., proteins encoded by the bacteria or virus).

The exogenous antigens are fragmented, and the fragments are presented on the surface of the antigen presenting cells (APCs) via class II major histocompatibility complexes (MHC II). The endogenous antigens are fragmented, and the fragments are presented on the surface of APCs via class I major histocompatibility complexes (MHC I). The antigen presentation via MHC I requires co-stimulation by the CD80 receptor present on the surface of the APCs and the antigen presentation via MHC II requires co-stimulation by the CD40 receptors present on the surface of the APCs.

Adjuvants can act in several ways:

1. By inducing surface expression of antigen presenting molecules such as MHC I and II on APCs, 2. By activating APC's and up-regulating expression of co-stimulatory molecules such CD40 and CD80, and/or, 3. By enhancing the release of cytokine and chemokine.

The in-vitro determination of the innate immune response can be evaluated by Griess's assay for nitrite. APCs release nitric oxide upon exposure to an antigen or a foreign invading pathogen. Nitric oxide is thus an important marker for an innate immune response. The release of nitric oxide (NO) can be quantified by measuring the concentration of its oxidation product nitrite via spectroscopic Griess's assay.

The in-vitro determination of adaptive immune response is done via flow cytometric analysis of the antigen presenting molecules (MHC I and MHC II) and co-stimulatory molecules (CD40 and CD80) that are expressed on the surface of the APCs upon stimulation with the microparticles.

Oral dissolving film formulation containing drug/vaccines (in this example, vaccine COVID-1 Spike S-1 protein antigen and the SARS CoV-2 virus) were successfully formulated.

Using the 3D printing technology, we were able to completely automate the ODF film formulation.

By taking advantage of the in-built UV lamp within the 3D printer, we were successful in crosslinking the film using the UV in as little as 45 seconds, with no degradation to the protein and thus the formulation of the ODF from start to end could be accomplished completely automatically within a timeframe of 3-5 minutes for each batch of 96 ODF films.

The in-built design of the laminar flow air system within the 3D printer was taken advantage of to formulate the ODF films aseptically.

The SEM demonstrated uniform distribution of the microparticles within the ODF film.

The addition of chitosan glutamate (Component 3) imparted excellent adhesive properties to the ODF. Good adhesive property is essential for ODF formulations. After application to the buccal cavity or after sublingual administration, ODF formulations need to be tacky enough to stick to the mucous surface long enough for the drug/vaccine antigen to be absorbed into circulation for soluble drugs or for particulate vaccine antigens, taken up by phagocytic cells (such as macrophages or dendritic cells) that are present in the mucous lining of the buccal cavity or sublingual membrane. Chitosan is known for its excellent mucoadhesive properties.

The disintegration time of the ODF containing the COVID-19 Spike S-1 protein, demonstrated about 50% breakup of the ODF within 5 minutes.

The release studies demonstrated about 50% release of the COVID-19 Spike S-1 protein within about 3 minutes, thereby making it available for absorption/uptake.

Applications of this method to test vaccines against COVID-19 demonstrated excellent immune responses after ODF administration.

ODF formulations allows for delivery to overcome the shortcomings of traditional vaccines including cold chain storage, patient compliance, and mass vaccination.

The Examples below demonstrate the successful formulation of ODF films aseptically, in a completely automated process, with no batch to batch variations, in a matter of 2 minutes from start to end, for a batch of 96 ODF films. This allows for large scale up of this manufacturing process for ODF, without any need of any modifications to the process.

One exemplary method of preparing ODFs of the present disclosure comprises generally the following Steps:

Step A: A solution is prepared of at least one film-forming agent, at least one crosslinking agent (such as, but not limited to, at least one polyethylene glycol), and at least one polar solvent (such as, but not limited to, alcohol, water, or the like; one solvent usable is ethanol).

In exemplary embodiments the film-forming agent can be any suitable alcohol-soluble polymer selected from the group consisting of polyvinylpyrrolidone (PVP), polyethylene glycol, or the like, or mixtures or combinations of one or more of the foregoing. Alternatively, in exemplary embodiments the film-forming agent can be any suitable water-soluble material, such as, but not limited to, albumin, gelatin, sugars, or the like, or mixtures or combinations of one or more of the foregoing. In one exemplary embodiment, the film-forming agent can be KOLLIDON™, a family of proprietary compositions containing PVP (available from BASF).

The crosslinking agent can be one or more materials which crosslink in the presence of ultraviolet light. In exemplary embodiments, the crosslinking agent can be polyethylene glycol diacrylate (PEGD) or other polyethylene glycol.

The solvent can be alcohol or water.

Step B: To this solution is added either a suspension or solution of at least one nano- or micro-encapsulated bioactive material in, for example, water, to form a mixture. Nano- or micro-encapsulated particles may be made according to one or more of the methods (as applicable and as appropriate) described in U.S. Pat. Nos. 6,555,110; 7,105,158; 7,425,543; 9,149,441; 10,004,790; and, 10,463,608, the disclosures of all of which are incorporated by reference herein.

Step C: To the mixture of Step B is added at least one photoinitiator. At least one surfactant can also be added.

The at least one photoinitiator (which initiates crosslinking of the crosslinking agent) can be any suitable material which initiates crosslinking upon exposure to radiation (e.g., UV or visible), such as, but not limited to, alpha-cleavable and the nocleavable classes of photoinitiators, which are molecules that creates reactive species (free radicals, cations, or anions). The photoinitiator can be at least one photoinitiator selected from the group consisting of azobisisobytyronitrile, camphoquinone, and benzoyl peroxide (commonly used industrial photoinitiators), and the like, and mixtures of at least two photoinitiators. In exemplary embodiments, di-phenyl-phosphene oxide is used as the photo-initiator At least surfactant, such as, but not limited to, TWEEN™ or SPANS is added to the alcohol-based solvent. In exemplary embodiments, a polysorbate, such as, but not limited to, TWEEN™ 20 and 80 (available from Sigma Aldrich) is used as the surfactant.

Step D: The mixture of step (b) above is added to a dispenser in a 3D printer. In exemplary embodiments the printer has the capability of exposing the tray to UV or visible light or other radiation In exemplary embodiments the exposure of the tray to radiation is done external to the printer.

Step E: In exemplary embodiments the printer dispenses the mixture of Step B into the wells of a conventional 12, 48 or 96 well (or other array arrangement) tray. In one exemplary embodiment the tray may have a single well. In exemplary embodiments the tray wells are open at the top and the bottom, and a removable backing film (which prevents the mixture from exiting the bottom of the wells) is adhered or otherwise associated with the bottom of the tray. One exemplary backing film is a film provided by 3M. The printer is programmed to dispense the mixture of step (b) into a plurality of wells in the tray.

Step F: The tray is exposed to UV light to promote the crosslinking of the at least one crosslinking agent in order for each well to have a film formed therein.

Step G: The tray of Step F is dried in a vacuum desiccator.

Step H: The backing film is removed from the tray and the films are removed and stored until ready for use or packaging.

In exemplary embodiments, the present disclosure provides an oral dissolving film including at least one drug, vaccine, or other bioactive material, comprising an oral dissolving film prepared according to any of the exemplary methods disclosed herein.

In exemplary embodiments, the present disclosure provides a material for delivering at least one drug, vaccine, or other bioactive material, comprising: a microencapsulated bioactive material formed into an oral dissolving film prepared according to any of the exemplary methods disclosed herein.

The following examples are set forth for purposes of illustration only. Parts and percentages appearing in such examples are by weight unless otherwise stipulated.

EXAMPLES

Oral Dissolving Films are film formulations intended for buccal or sublingual delivery of nano- or micro-encapsulated drugs or vaccines.

We tested several polymers to formulate ODF.

Initial formulation of ODF is shown in Table 1 below:

TABLE 1

| KOLLIDON 90F | 138 mg |
| KOLLIDON VA64 | 9 mg |
| PEG2000 | 5 mg |
| Absolute ethanol | 850 microliters |

The formulation process was automated using the 3D printer. The 3D printer was used to accurately dispense the film formulation, thus mitigating any manual errors.

Example 1

Example 1 describes a method of 3D-printing of an oral dissolving film using a 3D printer.

Figure 1:
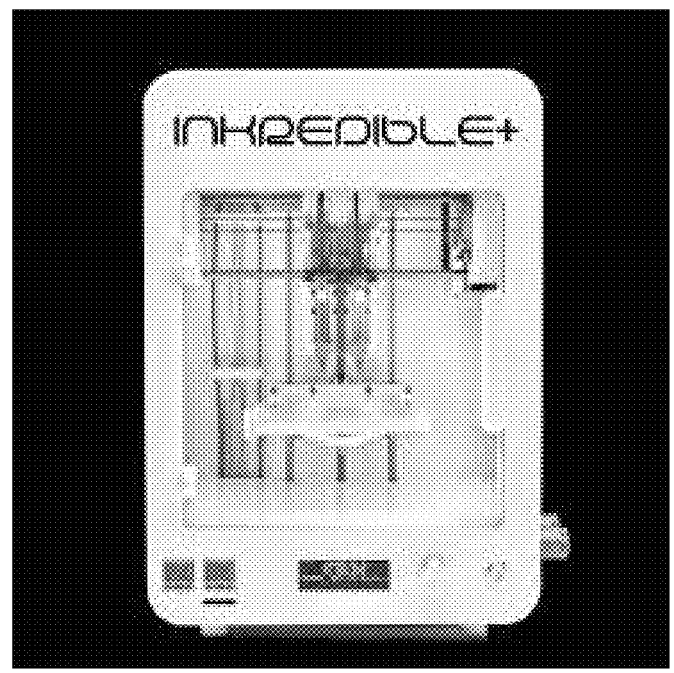
Figure 2:
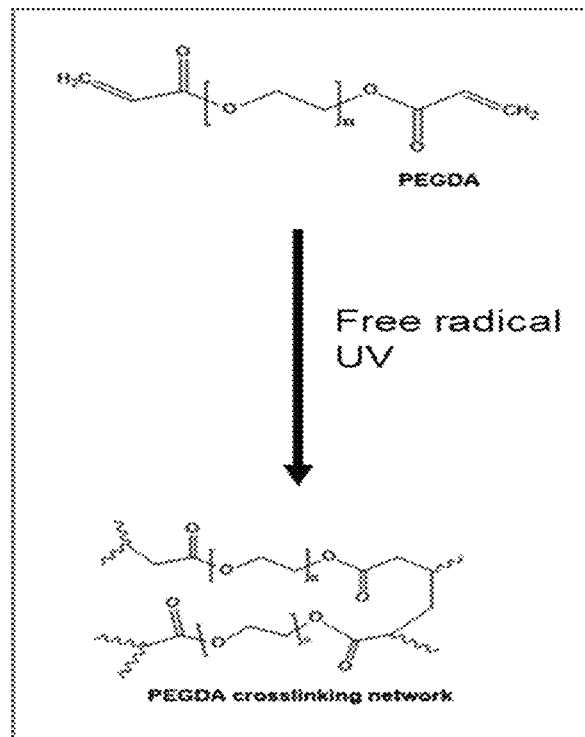
FIG. 2 is a pictorial view of a crosslinking reaction of poly(ethylene glycol)diacrylate (PEGDA) under UV light.

Method 1: 3D Printing of Oral Dissolving Film (ODF) using the CELLINK INKREDIBLE plus 3D printer A solution was first made of KOLLIDON™ 90F, KOLLIDON VA64, PEG2000 using Absolute ethanol in a beaker. This constitutes the film composition. To this was added the drug or vaccines in a nano or microparticulate suspension (solutions of the drugs or vaccine material can also be used alternatively). This suspension/solution was then added to one of the dispensers in a CELLINK INCREDIBLE Plus 3D printer (FIG. 1).

In this example we used the COVD-19 Spike S-1 protein as the vaccine antigen that was encapsulated into polylactic co-glycolic acid nanoparticles.

The 3D printer was then programmed to dispense into a 96 well format to conform to the 96-format mold to hold the ODF material.

We used the commercially available CELLINK INKREDIBLE plus 3D printer for the formulation of the film. The 3D printer has 2 printheads The film solution was then dispensed in the 96-format mold, and dried in the vacuum desiccator for 10 hours.

Example 2

Example 2 describes a method of 3D-an oral dissolving film printing using ultraviolet light crosslinking utilizing a UV lamp built into a 3D printer.

Method 2: 3D Printing using UV Crosslinking method using the inbuilt UV lamp in the CELLINK INKREDIBLE plus 3D printer A solution was first made of KOLLIDON 90F, KOLLIDON VA64, PEG2000 using Absolute ethanol in a beaker. This constitutes the film composition. To this was added the drug or vaccines in a nano or microparticulate suspension (solutions of the drugs or vaccine material can also be used alternatively). This suspension/solution was then added to one of the dispensers in the CELLINK INCREDIBLE Plus 3D printer (Cellink, Sweden).

The 3D printer was then programmed to dispense into a 96 well format to conform to the 96-format mold to hold the ODF material.

In this example we used the COVD-19 Spike S-1 protein as the vaccine antigen that was encapsulated into polylactic co-glycolic acid nanoparticles.

We used the commercially available CELLINK INK-REDIBLE plus 3D printer (FIG. 1) for the formulation of the film. The 3D printer has 2 different intensities of UV light 365 nm and 405 nm. It also has a HEPA filter for sterile manufacturing.

After the film was dispensed, the polymers were cured or cross-linked using the in-built UV lamp in the 3D printer. We used 405 nm UV wavelength for 45 seconds. The crosslinking reaction is illustrated in FIG. 2. Poly(ethylene glycol) diacrylate (PEGDA) is the pre-polymer solution that can be used in the formation of a cross-linked polymeric system. It readily crosslinks under UV light in presence of free radicals. We thus used PEGDA as the crosslinking polymer in the film formulation using the 3D printing technique. This allowed for very quick curing of the polymers to form the film using the 3D printing technique to completely automate the process.

Example 3

Example 3 describes a method of 3D-printing of an oral dissolving film using five components.

Variations of the film formulation with 5 different components, as illustrated in Table 2 below, were also tested:

TABLE 2

| Formulation | Component 1 | Component 2 | Component 3 | Component 4 | Component 5 |
|---|---|---|---|---|---|
| Formulation 1 | KOLLIDON 90F 138 mg KOLLIDON VA64 9 mg PEG2000 5 mg Absolute ethanol 850 microliters | PEGDA | Lactose DI water | Diphenyl phosphine oxide (photo-initiator) | Tween 20 (surfactant) |
| Formulation 2 | KOLLIDON 90F KOLLIDON VA64 PEG2000 Absolute ethanol | PEGDA | Gelatin DI water | Diphenyl phosphine oxide (photo-initiator) | Tween 20 (surfactant) |
| Formulation 3 | KOLLIDON 90F KOLLIDON VA64 PEG2000 Absolute ethanol | PEGDA | Sodium bicarbonate DI water | Diphenyl phosphine oxide (photo-initiator) | Tween 20 (surfactant) |
| Formulation 4 | KOLLIDON 90F KOLLIDON VA64 PEG2000 Absolute ethanol | PEGDA | Trehalose DI water | Diphenyl phosphine oxide (photo-initiator) | Tween 20 (surfactant) |
| Formulation 5 | KOLLIDON 90F KOLLIDON VA64 PEG2000 Absolute ethanol | PEGDA | Sucrose DI water | Diphenyl phosphine oxide (photo-initiator) | Tween 20 (surfactant) |
| Formulation 6 | KOLLIDON 90F KOLLIDON VA64 PEG2000 Absolute ethanol | PEGDA | Sucrose Chitosan glutamate DI water | Diphenyl phosphine oxide (photo-initiator) | Tween 20 (surfactant) |

Method 3:

The Components 1,2,3 were mixed in the ratio 2:1:1 (850 ul: 425 ul: 425 ul) while continuous stirring on the magnetic stirrer.

To this was added the drug or vaccines in a nanoparticulate or microparticulate suspension (solutions of the drugs or vaccine material can also be used alternatively). This suspension/solution was then added to one of the dispensers in the CELLINK INCREDIBLE Plus 3D printer.

In this example we used the COVD-19 Spike S-1 protein as the vaccine antigen that was encapsulated into polylactic co-glycolic acid nanoparticles Component 4 and 5, Tween 20 and Diphenyl phosphine oxide (photo-initiator) are then added into the mixture.

The films are then printed using the 3D printer. The films were formulated using a 96-station mold to formulate the films having the average diameter of about 3-4 mm. The fluorosilicone coated polyester film obtained from 3M was used as the backing membrane for formulation of the film.

Formulation 6 (from Table 2 above) was selected for further optimization.

Table 3 below shows formulation ratios:

TABLE 3

| Formulation | Ratio of mixing of component 1: component 2: component 3 |
|---|---|
| Formulation A | 1:7:2 |
| Formulation B | 1:6:2 |
| Formulation C | 1:5:2 |
| Formulation D | 1:4:2 |
| Formulation E | 1:3:2 |
| Formulation F | 1:2:2 |
| Formulation G | 1:2:3 |
| Formulation H | 1:1:2 |

TABLE 3-continued

| Formulation | Ratio of mixing of component 1: component 2: component 3 |
|---|---|
| Formulation I | 2:1:2 |
| Formulation J | 4:1:4 |
| Formulation K | 4:1:2 |
| Formulation L | 4:1:1 |
| Formulation M | 2:1:1 |

Formulation M was selected for further optimization based on the appropriate mixing of all the 3 components and ability of the film formulation to disintegrate in the artificial saliva.

Other parameters optimized for the formulation were as shown in Table 4 below:

TABLE 4

Concentration of photo-initiator
Distance between source of UV light and the film formulation
Intensity of UV light
Crosslinking time The lead formulation of ODF is shown in Table 5 below:

TABLE 5

| Component 1 | Component 2 | Component 3 | Component 4 |
|---|---|---|---|
| KOLLIDON 90F 16.24% w/v KOLLIDON VA64 1.06% PEG2000 0.6% w/v Absolute ethanol | PEGDA Mn 575 | Chitosan glutamate 1.5% w/v Sucrose 40% w/v Deionized water | Diphenyl phosphine oxide 0.02% w/v Tween 20 |

3D Printer settings used are shown in Table 6 below:

TABLE 6

| Distance between source of UV light and film | 6 cm |
|---|---|
| Intensity of UV light | 405 nm |
| Crosslinking time | 45 sec |

Example 4

Characterization of the ODF Films

Figure 3A:
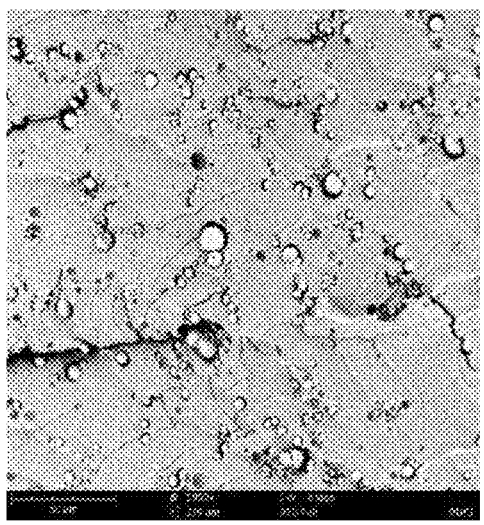
FIG. 3A is a SEM (scanning electron microscope) image of the ODF loaded with microparticles.
Figure 3B:
FIG. 3B is a cross-section of the ODF of FIG. 3A under light microscope.

The film loaded with the microparticles was visualized using light and scanning electron microscopy (SEM) (FIG. 3A) and the cross-section of the film was visualized under the light microscope (FIG. 3B).

Example 5

Adhesive Testing

Figure 4:
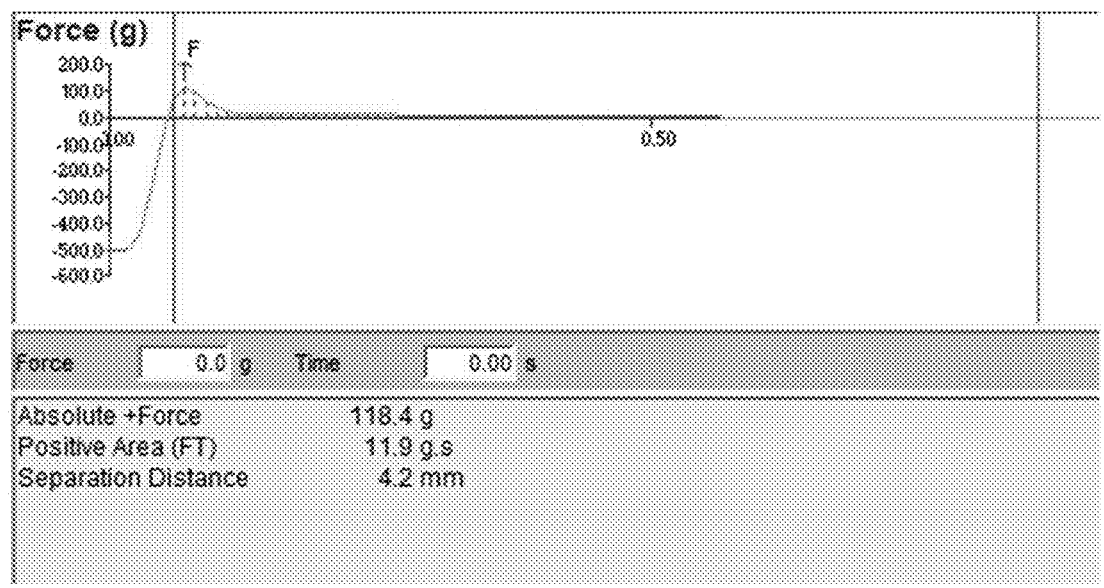
FIG. 4 is a graph of adhesive testing of the film.

The adhesive property of the film was tested using TA.XT plus texture analyzer (Chem Instruments) (FIG. 4). Tack test confirming the excellent adhesive behavior of the ODF. This was probably imparted by chitosan glutamate, which has excellent mucoadhesive properties.

Example 6

Figure 5A:
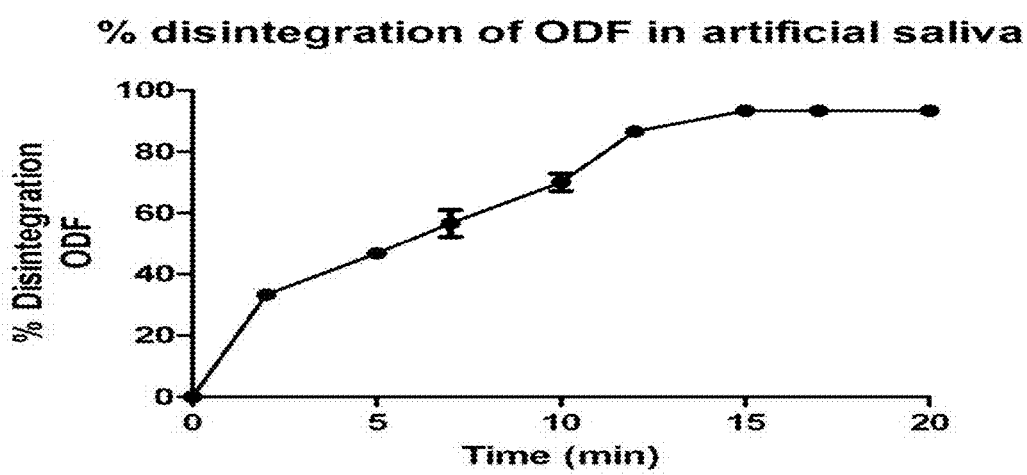
FIG. 5A is a graph of percent disintegration of ODF in artificial saliva.
Figure 5B:
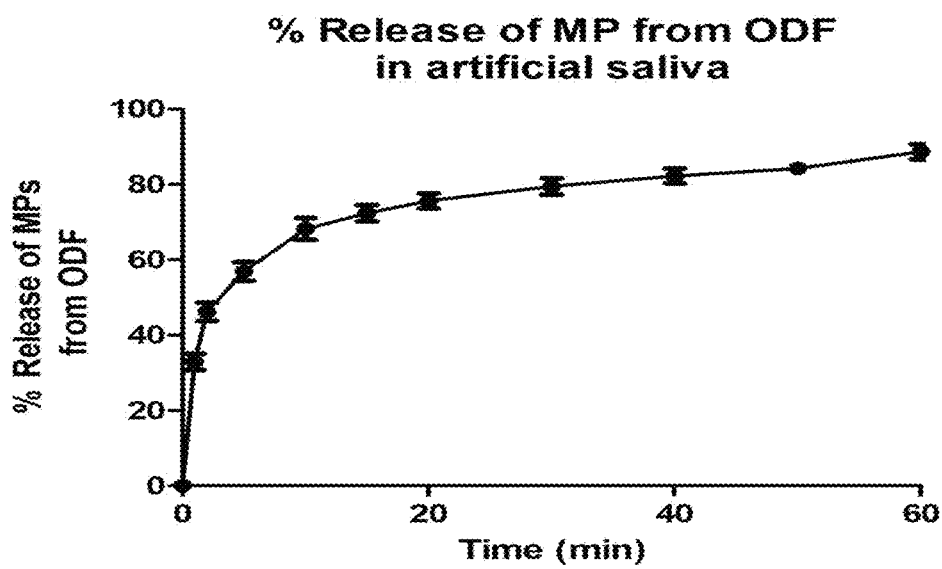
FIG. 5B is a graph of percent release of microparticles (MP) from ODF in artificial saliva.

Disintegration of the ODF and Percentage Release of COVID-19 vaccine antigen from Microparticles in the ODF Film Formulation:

Percent disintegration of the film and percent release of the antigen from the microparticles loaded in the film formulation was evaluated in the artificial saliva as the medium at 37 C (FIG. 5A, 5B). Percent disintegration of the ODF film (FIG. 5A) and percent release of the microparticles containing COVID-19 as the vaccine antigen (FIG. 5B) from the microparticles loaded in the film formulation was evaluated in the artificial saliva as the medium at 37 C.

Example 7

We have evaluated two different ODF formulations (1) COVID-19 SARS CoV-2 inactivated virus and (2) Spike S-1 protein vaccine.

ODF vaccines of SARS-CoV-2 virus and the Spike S-1 protein were nontoxic and demonstrated excellent immunogenicity in cell culture studies.

Figure 6A:
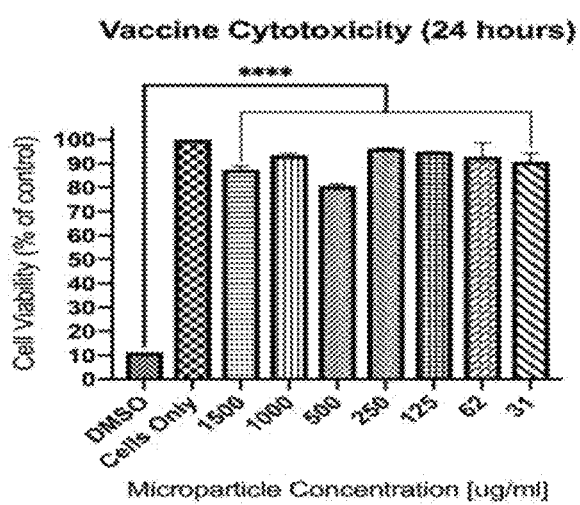
FIG. 6A is a chart of ODF toxicity studies.

We prepared preliminary batches of intact heat inactivated SARS-CoV-2 virus (ATCC, VA), and Spike S-1 protein, (Genscript, NJ), encapsulated into ODF film formulations as described earlier (Method 3). The vaccine antigen (2.5%) and adjuvants (Alum, MF-59, MPL-A, or their combinations, 2.5%) were also evaluated. The ODF films were characterized for their surface morphology and toxicity. The ODF were tested for toxicity by exposing them to dendritic cells (DC) in culture: all studies demonstrated greater than 95% cell viability (N=6 batches, FIG. 6A). Our studies in non-human primates with similar biodegradable matrices, demonstrated no in-vivo liver or kidney toxicity as demonstrated by serum creatinine, BUN, and SGOT levels.

Figure 6B:
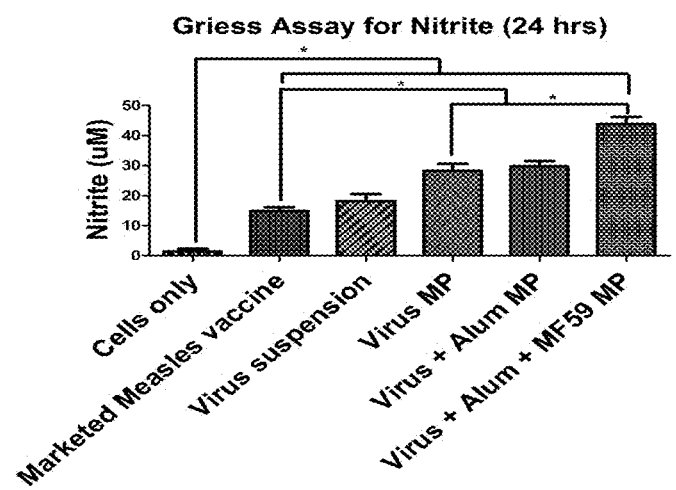
FIG. 6B is a chart of a Griess Assay for Nitrite after exposure of the ODF Spike S-1 film or ODF containing SARS-CoV-2 virus demonstrated strong innate immunogenicity ($*p<0.05$).

The enhanced nitrite release after exposure of the ODF containing Spike S-1 particulate vaccines (with adjuvants such as Alum or MF59) to dendritic cells, was significantly higher when comparable to a marketed measles vaccine at equivalent doses (FIG. 6B).

Figures 7A, 7B, 7C, 7D:
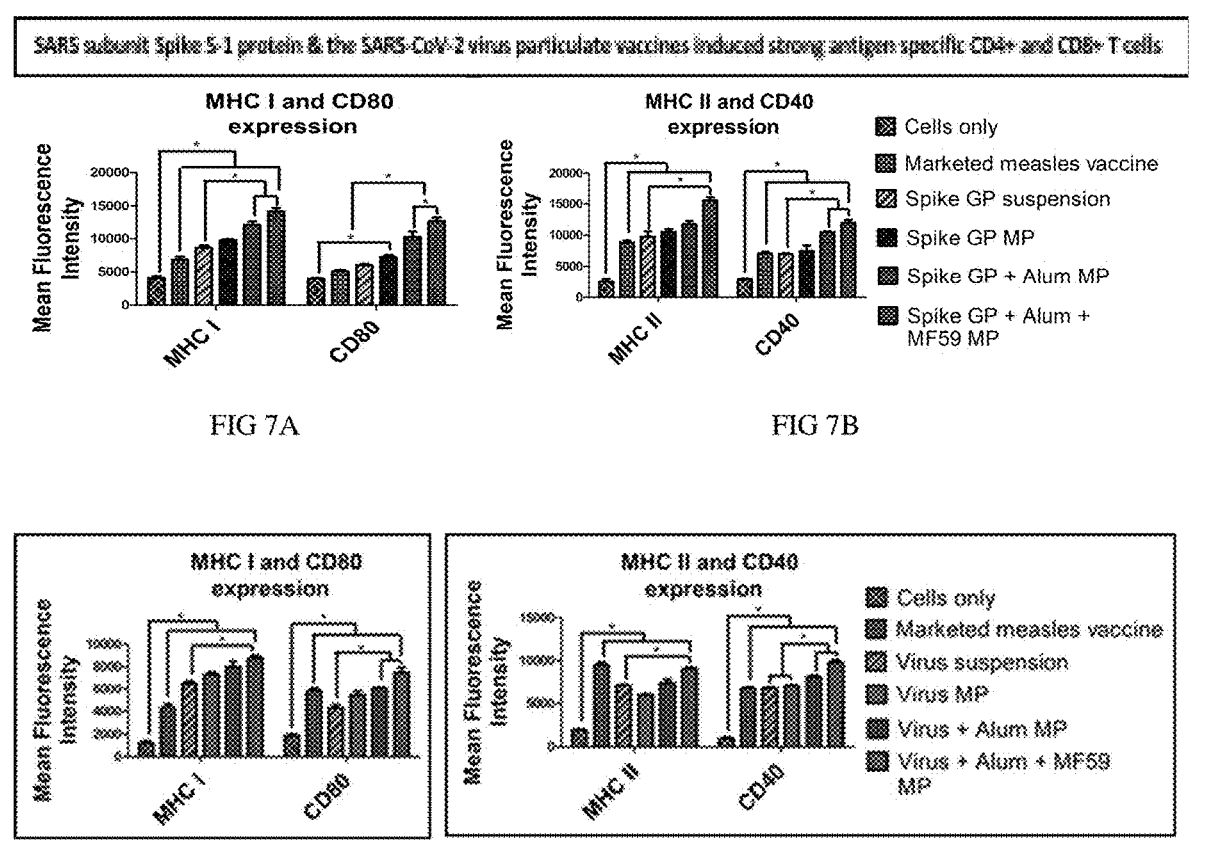

Further, as a measure of innate immune responses, levels of cytokines such as TNF-alpha, IL-1beta and IFN-gamma levels were higher in DC exposed to vaccine particles, demonstrating significantly higher immunogenicity when compared to non-encapsulated vaccine virus or spike S-1 proteins or controls. Also, both the ODF containing the encapsulated vaccines (heat inactivated virus and spike S-1 protein) enhanced both MHC-I and MHC-II and their corresponding CD-80 and CD-40 co stimulatory molecules in studies carried out using dendritic cells (DC2.4) as determined by FACS analysis (FIG. 7). Interestingly, the MHC-I and MHC-II and their corresponding CD-80 and CD-40 co stimulatory molecules were also significantly higher than equivalent does of the marketed measles vaccine (p<0.01) with Spike S-1 protein vaccine (FIG. 7, A, B) and SARS virus vaccine. (FIG. 7, C, D). The adjuvanted particulate vaccines in most cases resulted in significantly higher responses than non-encapsulated vaccine particles.

We further evaluated the time taken for the ODF to dissolve and release the vaccine antigen once administered transdermally. FIG. 8B represents the release kinetics of the Spike protein from the ODF matrix, showing about 50% release in about 60 hours, demonstrating excellent sustained release of the vaccine antigen. FIG. 8A represents the release profile of the Spike protein from the ODF, showing that about 50% was released within about 62 hours, indicating that the release of the vaccine antigen was controlled mostly by the release from the microparticle matrix and that the ODF themselves did not further delay the antigen release.

Example 8

Preliminary pre-clinical studies in mice targeting ODF to the buccal cavity induces protective immunity.

We successfully developed ODF based formulations and the results of the SARS CoV-2 Spike S-1 protein and inactivated virus are discussed below.

We recently also conducted some preliminary studies in mice (n=3 mice/group), using ODF of either the SARS-CoV-2 Spike S-1 protein or the inactivated SARS-CoV-2 virus as the vaccine antigens in separate studies. For in vivo studies, 6-8 weeks old mice were obtained from Charles River Laboratories, MA. The animals are administered with an ODF film at day 0 onto the buccal cavity prime. Serum antigen specific antibody titers were determined at baseline and weeks 4 and 12. We obtained significantly higher IgG titers in the mice that received the Spike protein or the inactivated virus when administered using ODF in the buccal cavity as compared to traditional i.m. administered vaccine suspension or microparticles at week 12 after a single ODF formulation administration (FIG. 9).

We obtained excellent CD4 and CD8 T-cell responses in the lymph nodes of the mice vaccinated with the ODF, shown in FIGS. 10A and 10B which shows Spike S-1 and SARS-CoV-2 Heat Inactivated Virus induced serum IgG levels. The mice received one vaccine dose at week 0. Either as the antigen in suspension/solution or in microparticles or microparticles in ODF. Serum IgG was determined at week 4 and 12. The ODF group receiving particulate vaccines showed IgG levels significantly higher than the corresponding suspension vaccinated mice (*p<0.01 from suspension group). [S-1=SARS CoV-2 Spike S-1protein; Susp.=SARS CoV-2 Virus Suspension; MP=Microparticles, ODF=oral dissolving film].

Likewise, excellent CD4 and CD8 T-cell responses in the spleen were noted in the mice vaccinated with the ODF (FIGS. 11A and 11B). We were also interested in determining if the vaccine the long-term memory responses after a single ODF administration. Thus, we determined the CD27 (memory B cell), CD45R (memory T cell) and CD62L (central T cell) responses in the spleen and lymph nodes of mice sacrificed at the end of the study, which were significantly higher in all the vaccine groups. This data is encouraging since it demonstrates that there is a good potential that a single ODF patch might be sufficient. The addition of adjuvants could possibly enhance immunogenicity even further by significantly improving antigen presentation.

Although only a number of exemplary embodiments have been described in detail above, those skilled in the art will readily appreciate that many modifications are possible in the exemplary embodiments without materially departing from the novel teachings and advantages. Accordingly, all such modifications are intended to be included within the scope of this disclosure as defined in the following claims.

While the methods, equipment and systems have been described in connection with specific embodiments, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods, equipment and systems. These and other components are disclosed herein, and it is understood that when combinations, subsets, interactions, groups, etc., of these components are disclosed that while specific reference of each various individual and collective combinations and permutation of these may not be explicitly disclosed, each is specifically contemplated and described herein, for all methods, equipment and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

It should further be noted that any patents, applications and publications referred to herein are incorporated by reference in their entirety.

What is claimed is:

1. A method of producing oral dissolving films containing at least one nano- or micro-encapsulated bioactive material, the method comprising:
   a) preparing a solution of at least one film-forming agent, at least one crosslinking agent, and at least one polar solvent;
   b) adding to the solution of step (a) either a suspension or solution of at least one nano- or micro-encapsulated bioactive material to form a mixture;
   c) adding to the mixture of step (b) at least one surfactant and at least one photoinitiator to form a mixture;
   d) dispensing the mixture of step (c) by a 3D printer into a tray having at least one well formed therein; and,
   e) exposing the tray to radiation to initiate crosslinking so as to promote formation of a film in each well.

2. The method of claim 1, further comprising a step (f) drying the tray.

3. The method of claim 1, further comprising a step (g) removing a removable backing associated with a bottom defined by the tray to prevent liquid from exiting the tray.

4. An oral dissolving film including at least one drug, vaccine, or other bioactive material, comprising an oral dissolving film prepared by the method of claim 1, wherein the oral dissolving film is configured to stick to a mucous surface for a time sufficient to allow the at least one drug, vaccine, or other bioactive material to be taken up by phagocytic cells that are present in a mucous lining of a buccal cavity.

5. The oral dissolving film of claim 4, wherein the film has sustained release of 50% in 60 hours.

6. A material for delivering at least one drug, vaccine, or other bioactive material, comprising: an oral dissolving film comprising a microencapsulated bioactive material, the film prepared according to the method of claim 1, wherein the material is configured to stick to a mucous surface for a time sufficient to allow the at least one drug, vaccine, or other bioactive material to be taken up by phagocytic cells that are present in a mucous lining of a buccal cavity.

7. The method of claim 1, wherein the at least one microencapsulated bioactive material comprises a vaccine antigen.

8. The method of claim 1, wherein the at least one film-forming agent comprises an alcohol-soluble polymer.

9. The method of claim 1, further comprising adding an adhesive to the film to increase tack thereof.

10. The method of claim 9, wherein the adhesive further comprises chitosan glutamate.

11. The method of claim 1, wherein the tray is exposed to ultraviolet light.

12. The method of claim 1, wherein the cross-linking agent comprises poly(ethylene glycol) diacrylate (PEGDA).

\* \* \* \* \*